United States Patent [19]

Shasha et al.

[11] 4,344,857
[45] Aug. 17, 1982

[54] ENCAPSULATION BY ENTRAPMENT

[75] Inventors: Baruch S. Shasha, Peoria; William M. Doane, Morton, both of Ill.; Charles R. Russell, deceased, late of Peoria, Ill., by Kathleen G. Russell, heir

[73] Assignee: The United States of America as represented by the Secretary of Agriculture, Washington, D.C.

[21] Appl. No.: 150,550

[22] Filed: May 16, 1980

Related U.S. Application Data

[63] Continuation-in-part of Ser. No. 733,968, Oct. 19, 1976, Pat. No. 4,277,364, which is a continuation-in-part of Ser. No. 642,836, Dec. 22, 1975, abandoned.

[51] Int. Cl.$^3$ .................... B01J 13/02; A01N 25/26
[52] U.S. Cl. .................... 252/316; 71/3; 71/66; 71/100; 71/117; 71/64.11; 424/19; 424/22; 424/35; 424/213; 424/214; 424/354
[58] Field of Search .......... 252/316; 71/64.11, 66, 71/100, DIG. 1; 424/19, 22, 35, 214

[56] References Cited

U.S. PATENT DOCUMENTS

| | | | |
|---|---|---|---|
| Re. 29,238 | 5/1977 | Dimitri et al. | 71/DIG. 1 |
| 3,160,552 | 12/1964 | Russell et al. | 536/103 X |
| 3,247,066 | 4/1966 | Milosovich, Jr. | 424/37 X |
| 3,576,660 | 4/1971 | Bayless et al. | 252/316 X |
| 3,576,760 | 4/1971 | Gould et al. | 424/32 X |
| 3,669,722 | 6/1972 | Bishop | 428/402 |
| 3,778,383 | 12/1973 | Schibler et al. | 252/316 |
| 4,277,364 | 7/1981 | Shasha et al. | 252/316 |

FOREIGN PATENT DOCUMENTS

| | | | |
|---|---|---|---|
| 1163023 | 9/1969 | United Kingdom | 252/316 |

OTHER PUBLICATIONS

Iwasaki et al: "The Decomposition of Xanthate in Acid Solution", J. Am. Chem. Soc. 80: 285–288 (1958).
Kirk-Othmer, *Encyclopedia of Chemical Technology*, 2nd Ed., vol. 17, pp. 178–180 (1963).
S. Ramachandra Rao, Xanthates and Related Compounds, Marcel Dekker, Inc., N.Y., pp. 63–77 (1971).

*Primary Examiner*—Richard D. Lovering
*Attorney, Agent, or Firm*—M. Howard Silverstein; David G. McConnell; Curtis P. Ribando

[57] ABSTRACT

Chemical biological agents to be encapsulated are dissolved or dispersed in an aqueous solution of polyhydroxy polymer xanthate. Simultaneous addition of a strong acid and a coupling agent to the solution insolubilizes the polyhydroxy polymer without degrading the xanthate moiety, thereby entrapping the agents in a protective matrix. Encapsulation of biologically active compositions provides a shield against hostile environments, improves safety in handling, and slows the release of such compounds to the surrounding medium. Highly volatile liquids are protected against losses by evaporation. Encapsulation also provides protection against decomposition from exposure to ultraviolet light.

9 Claims, No Drawings

ENCAPSULATION BY ENTRAPMENT

CROSS-REFERENCES TO RELATED APPLICATIONS

This is a continuation-in-part of Ser. No. 733,968 filed Oct. 19, 1976, now U.S. Pat. No. 4,277,364 which in turn is a continuation-in-part of Ser. No. 642,836 filed Dec. 22, 1975, now abandoned.

BACKGROUND OF THE INVENTION

1. Field of the Invention

The invention relates to a method of encapsulating materials by entrapment in a matrix of water-insoluble polyhydroxy polymers and to the compositions prepared thereby.

2. Description of the Prior Art

Prior art methods of encapsulation can be described in two major categories, physicomechanical and chemical. Physicomechanical techniques include the following: spray drying; dipping or centrifuging technique; multiple nozzle spraying; fluidized bed coating; electrostatic microencapsulation; and vacuum encapsulation. The most important chemical encapsulation techniques include simple and complex coacervation and interfacial polymerization. A detailed description of coacervation and the above-mentioned physicomechanical techniques is given in the background of the parent application. The interfacial polymerization method necessitates the use of at least a two-phase system. One of the reactants must be soluble in the continuous phase and insoluble in the discontinuous phase (core material). The other reactant must be insoluble in the continuous phase and soluble in the discontinuous phase. The polymerization reaction occurs at the interface between the two phases forming a polymer shell around the core material, thereby completely enveloping it. This shell must be insoluble in both phases. In this method either phase can be an aqueous system. See U.S. Pat. No. 3,577,515 and 3,575,882 and British Pat. No. 1,163,023.

The above encapsulation methods are multistep processes which require carefully controlled conditions or special equipment. They are time consuming and expensive, often requiring elevated temperatures and pressures other than ambient; and they all require at least a two-phase system. Many require expensive, toxic, and flammable solvents which must be recovered. Coacervation is limited to the encapsulation of oils in materials which have the capacity to form gels. Interfacial polymerization techniques, also requiring two or more phases, are limited essentially to expensive synthetic polymerization systems, many of which are petrochemicals and which generally produce nonbiodegradable polymers. To make these systems more economical and to prevent ecological contamination, unreacted monomers must be recovered. The only system that appears to be useful for coating solid particles is the fluidized bed technique.

SUMMARY OF THE INVENTION

In contrast to prior art encapsulation systems, the chemical encapsulation method that we have discovered has the advantage of operating not only in aqueous and nonaqueous two-phase systems, but also in single-phase systems in which a matrix-forming material and core material are soluble in the same solvent. The encapsulation system is also operative for water-insoluble liquids and solid particulate core material dispersed in the aqueous solution of matrix-forming material. The method of the invention uses neither the coacervation nor the interfacial polymerization techniques but is a method of encapsulating a substance by quickly insolubilizing a polyhydroxy polymer xanthate in the presence of suitable core material which is thereby entrapped within the insolubilized matrix. The method operates at ambient temperatures and pressures.

The method comprises the following steps:

a. preparing a dispersion or solution of a suitable chemical biological agent in a matrix-forming material comprising an aqueous solution of a polyhydroxy polymer xanthate (PPX) having a xanthate degree of substitution of from about 0.1 to 3, wherein the solution has a concentration of PPX of from about 5–70%, and wherein the relative amount of said PPX with respect to said biological agent is sufficient to entrap said agent within a matrix of said PPX;

b. simultaneously adding to said dispersion a strong acid and a coupling agent selected from the group consisting of hydrogen peroxide, ferric sulfate, and ferric chloride, whereby the dispersion is adjusted to a pH of from about 2 to about 7 and whereby said PPX and said coupling agent react from a single phase to form an insolubilized matrix thereby entrapping said agent; and c. recovering said entrapped chemical biological agent.

The method of the invention has the advantage of encapsulating both volatile and nonvolatile core materials. Core materials can be either liquid or finely divided solids, organic or inorganic, polar or nonpolar. If a two-phase system is used, it is not necessary to form an emulsion. Simple hand mixing of the components is sufficient.

It is an object of the invention that the encapsulating materials be generally less expensive than those used in the prior art and be inclusive of those derived from natural, renewable resources.

It is also an object of the invention to sufficiently entrap biologically active chemicals in a matrix to increase the safety in handling them, to slow their release to the environment, and to reduce losses due to volatility and decomposition by sunlight.

DETAILED DESCRIPTION OF THE INVENTION

Polyhydroxy polymer xanthates (PPX) suitable for use in accordance with the invention are prepared from any natural or synthetic polyhydroxy polymer capable of forming xanthate derivatives of suitable xanthate degree of substitution (D.S.) including starches, starch fractions (e.g., amylose and amylopectin), methyl starch, hydroxyethyl starch, cereal flours (e.g., from whole wheat, bran, refined wheat, and wheat fractions), depolymerized flours, cellulose, methyl cellulose, hydroxyethyl cellulose, dextrin, dextran, guar gum, bipolymers (e.g., xanthan gum), cationic starch, anionic starch, and synthetic poly alcohols (e.g., polyvinyl alcohol). Suitable xanthate D.S.'s fall within the range of from 0.1 to 3, preferably from 0.1 to 1. The PPX is employed as an aqueous system, wherein the operable range of PPX concentration for effective matrix formation is from about 5% to about 70%, with a range of 10% to 50% being preferred.

The reaction by which the PPX is insolubilized to form the matrix around the core materials is fully described in commonly assigned U.S. Pat. No. 3,160,552 and by Russell et al., Tappi 45(7):557–566 (July 1962) which are herein incorporated by reference. Heretofore the reaction of certain PPX compositions with coupling compounds, as described in the above references, has been essentially confined to the preparation of paper having increased wet and dry strengths, to paper coatings, and to reinforced rubbers (U.S. Pat. No. 3,830,762). Suitable coupling agents are contained in three basic categories: oxidative coupling agents which include sodium nitrite, nitrous acid, iodine, chlorine, sodium tetrathionate, cyanogen bromide, nitrosyl chloride, chloramine T, and hydrogen peroxides; polyvalent metal ion coupling agents which include water-soluble salts of $Hg^{+2}$, $Fe^{+2}$, $Fe^{+3}$, $Zn^{+2}$, $Cu^{+2}$, $Cd^{+2}$, $Pb^{+2}$, $Mn^{+2}$, $Ni^{+2}$, and $Cr^{+3}$; and difunctional coupling agents such as alkyl dihalides, diepoxides, and epihalohydrins. Examples of the dihalides are dibromomethane, dibromopropane, and dichlorobutane. Examples of the diepoxides are 1,2:3,4-diepoxybutane, 1,2:4,5-diepoxypentane, and 1,2:7,8-diepoxyoctane. Examples of the epihalohydrins are epichlorohydrin and epibromohydrin. The basic matrix structures resulting from each of the above categories of coupling agents are (1) a polyhydroxy polymer disulfurdicarbothionate, (2) a polyvalent metal dithiocarbonate of a polyhydroxy polymer, or (3) an alkyl dithiocarbonate of a polyhydroxy polymer, as depicted below:

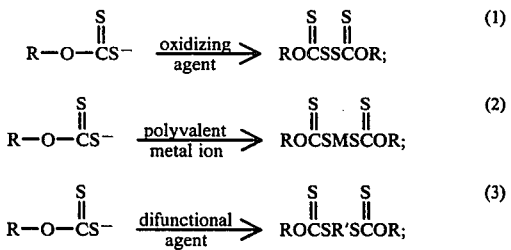

where M=polyvalent metal ion; R=polyhydroxy polymer; and R'=alkyl or substituted alkyl.

It is to be understood that the alkyl or substituted alkyl in structure (3) above is derived from the specific difunctional coupling agent employed. Other coupling agents which will be considered suitable for use in accordance with the invention will be known to those skilled in the art.

PPX solutions are inherently alkaline. Reactions of PPX with coupling agents to form an insolubilized matrix usually require a pH of from about 2 to about 7, though a pH of from 4 to 7 is preferred. Because strong acids are notorious for the degradation of xanthates [Kirk-Othmer, *Encyclopedia of Chemical Technology*, 2nd ed., Vol. 17, pp. 178–180 (1963); S. Ramachandro Rao, *Xanthates and Related Compounds*, Marcel Dekker, Inc., N.Y. (1971)], the most obvious choice for an acidifying agent would be acetic acid or some other weak acid. However, we have surprisingly found that a strong acid may be employed if paired with a coupling agent selected from the group of hydrogen peroxide, ferric sulfate, or ferric chloride, and if added to the aqueous PPX system simultaneously with the coupling agent. The addition is preferably effected by premixing the acid and the coupling agent, or alternatively they may be mixed into the system as separate, but simultaneous, streams. Exemplary strong acids for use in this embodiment are sulfuric acid, hydrochloric acid, nitric acid, and phosphoric acid. Besides the economic advantages of acidifying with strong acids as opposed to weak acids, the resultant encapsulated product has a lower bulk density, thereby affording a better coverage per field area unit. If the acidifying agent is a weak acid, the order of addition of coupling agent and pH adjustment is not critical for most coupling agents. However, when sodium nitrite is used in combination with a weak acid, it is preferable to adjust the pH of the reaction medium after the coupling agent has been added, and with hydrogen peroxide it is preferable to adjust the pH first.

The resulting matrix may then be washed, filtered, and dried by any conventional method. The matrix washing can be with water or any other solvent that does not dissolve or react with the matrix material without loss of core material. However, after the matrix has been dried to yield a friable granular or powdered material, rewetting initiates biodegradation of the matrix material and release of the core material begins.

The usual reaction parameters of the above reaction (i.e., ambient temperature, pressure, etc.) are all well known to those skilled in the art and will not be considered herein.

Core materials to be encapsulated and suitable for use in accordance with the invention include any organic and inorganic solid capable of being finely divided or liquid that is water soluble, water insoluble, or water dispersible that does not interfere with the encapsulating process and does not react with or dissolve the encapsulating matrix.

Suitable chemical-biological agents are defined herein as including essentially all known herbicides, insecticides, fungicides, nematocides, bacteriocides, rodenticides, moluscides, acaricides, larvacides, animal, insect, and bird repellants, plant growth regulators, fertilizers, pheromones, sex lures and attractants, and flavor and odor compositions. Suitable examples of herbicides include S-propyl dipropylthiocarbamate, $\alpha,\alpha,\alpha$-trifluoro-2,6-dinitro-N,N-dipropyl-p-toluidine, N-butyl-N-ethyl-$\alpha,\alpha,\alpha$-trifluoro-2,6-dinitro-p-toluidine, S-ethyl diisobutylthiocarbamate, 2,6-dichlorobenzonitrile, 1,1'-dimethyl-4,4'-bipyridinium dichloride, 2,4-dichlorophenoxy acetic acid, sodium 2,4-dichlorophenoxy acetate, ammonium 3-amino-2,5-dichlorobenzoate, and 3-amino-2,5-dichloromethylbenzoate. Suitable examples of nematocides include 1,2-dibromo-3-chloropropane. Suitable examples of suitable insecticides include O-ethyl-S-phenylethyl phosphorodithioate, S-(1,2-dicarbethoxyethyl)-O,O-dimethyl dithiophosphate, methyl O,O-dimethyl-o,p-nitrophenyl phosphorothioate, 1,1,1-trichloro-2,2-bis(p-chlorophenyl), and 2,3-dihydro-2,2-dimethyl-7-benzofuranyl methyl carbamate. Suitable sex lures or attractants include methyl 4-allyl-2-methoxyphenol and tertiarybutyl 4-chloro-2-methyl cyclohexane carboxylate. For comprehensive lists of suitable pesticide compositions see O. Johnson, Chemical Week, pp. 39–64, June 21, 1972. Other compositions suitable as core materials for use in accordance with the invention will be known to those skilled in the art. Core materials dissolved in water-immiscible solvents and compatible combinations of the above types of compositions are also easily encapsulated by the instant method.

Effective amounts of core materials depend entirely on the type and characteristics of the core material, on matrix thickness, and on intended utility of the product.

A very volatile liquid would require a thicker or a more impermeable matrix structure than a nonvolatile solid. A volatile liquid to be used as a slow-release pesticide, for example, would require less matrix material than a volatile liquid to be completely withheld from the environment. In the latter instance a subsequent coating with an impermeable polymer, such as those disclosed in the prior art, could be applied to the instant product as discussed below. Matrix thickness is also controlled by a second coating of PPX. This is accomplished by resuspending the first insolubilized encapsulated product in a solution of PPX, and adding the coupling agent and acidifying agent to form a second matrix in the same manner as the first matrix. Additional coatings are applied in the same manner to build up the desired matrix thickness.

Release characteristics of matrix materials may also be altered by treating the instant product with a combination of resorcinol and formaldehyde, or other hardening agents as well known in the art. The hardening agents may be added to the matrix material before, during, or after insolubilization. Not only is the release of core materials from the instant product slowed on treatment with resorcinol and formaldehyde, but also this treatment facilitates dewatering and filtration of the instant product. The effective range of hardening agent concentration is from about 0.1% to about 10%, based on the dry weight of the PPX, with a range of 2% to 5% being preferred.

Release characteristics may also be modified by combining PPX with other materials such as rubber latexes. Without limitation thereto, examples of rubber latexes useful for combining with PPX include styrene-butadiene (SBR), styrene-acrylonitrile-butadiene, acrylonitrile-butadiene, isoprene, isoprene-acrylonitrile, isoprene-butadiene, and chloroprene (neoprene). PPX-latex combinations have been found to be effective as matrix-forming materials in first encapsulations as well as subsequent encapsulations. Rubber latexes can also be used alone as coating materials for the PPX matrix. The preferred range of ratios of rubber latex:total amount of PPX is from about 4:1 to about 1:9 by dry weight. Further modification of release properties of the PPX-rubber latex combinations may be achieved by incorporating effective amounts of rubber curing agents and curing accelerator agents, such as sulfur, carbon disulfide, butyl 8, and others as known in the art. Addition of such agents to the material mixture prior to matrix insolubilization is preferred.

In still another embodiment, the release characteristics of matrix materials may be altered by adding to the solution of PPX a synthetic polymer dissolved in an organic solvent. Most synthetic polymers are operable for this purpose, particularly the polyvinyl and polyacrylic types. Without desiring to be limited to any particular species, examples of suitable polymers are polystyrene, polyethylene, poly(vinyl chloride), and poly(methyl methacrylate). The polymer is dissolved in any suitable organic solvent as known in the art, such as benzene or toluene. Such PPX-organic soluble synthetic polymer combinations can be used as matrix-forming materials in first and/or subsequent encapsulations. The amount of synthetic polymer can range from 0–30%, dry weight basis, of the matrix combination, the preferred range being 1–25%. Alternatively, the organic soluble synthetic polymers can be used alone as a coating for the PPX matrix. The rubber latexes discussed above can also be incorporated to yield matrix-forming materials comprising PPX-organic soluble synthetic polymer-rubber latex combinations.

An effective amount of a suitable biological agent is defined herein as that amount of core material which will achieve the desired result (e.g., attract, repel, or kill pests, give off a detectable aroma or flavor, or enhance the growth of plants) when the encapsulated composition containing the effective amount of the suitable biological agent is placed in the proper environment. For purposes of sufficient entrapment within the matrix, it is preferred that the suitable chemical biological agent is present in the matrix-forming material before the encapsulating reaction in an amount equal to from about 1% to about 100% of the total amount of matrix-forming material on a dry weight basis. The resulting composition of matter, therefore, preferably contains a biological agent in amounts of from 1% to 50% of the total weight of the composition of matter on a dry weight basis.

The release of the biological agent requires that the environment in which the encapsulated composition is placed contains moisture. Fields, gardens, and the like in which pesticides, attractants, repellants, plant growth regulators, and fertilizers are normally used contain sufficient natural or added moisture to cause the release of the chemical biological agent. Odor and flavor compositions, which are used in foods, are released from the encapsulating matrix by moisture contained in or added to the food product. While not desiring to be bound to any particular theory, it is believed that the mechanism of release is effected by the biodegradation of the PPX matrix as well as by displacement by water and diffusion through imperfections in the matrix.

The following examples are intended to further illustrate the invention and should not be construed as limiting the invention which is defined by the claims. All parts and percentages herein are by weight unless otherwise specified.

EXAMPLE 1 a. Starch, 162 parts, was suspended in 1000 parts of water. Carbon disulfide, 36 parts, and 40 parts sodium hydroxide in 345 parts water were added to the starch suspension. The suspension was stirred and allowed to stand for 30 minutes at 25° C. to yield a starch xanthate (D.S. 0.35) solution having a concentration of 13.7%.

b. The procedure described in (a) above was repeated with 324 parts of starch in 2600 parts of water, 24.3 parts of carbon disulfide, and 40 parts of NaOH in 345 parts of water. The reaction mixture was allowed to stand for 1 hour at 25° C. to yield a starch xanthate (D.S. 0.1) having a concentration of 12.9.

c. The procedure described in (a) above was repeated with 32 parts of starch in 150 parts water, 25 parts carbon disulfide, and 32 parts NaOH in 110 parts water. The reaction mixture was allowed to stand for 1 hour at 25° C. to yield a starch xanthate (D.S. 1.0) having a concentration of 16%.

d. The procedure described in (a) above was repeated with 32.4 parts of starch in 100 parts water, 2.4 parts carbon disulfide, and 4 parts NaOH in 56 parts water. The reaction mixture was allowed to stand 1 hour at 25° C. to yield a starch xanthate (D.S. 0.1) solution having a concentration of 21.2%.

e. One hundred eighty parts of acid-modified corn flour—90 fluidity—were mixed with 180 parts of water followed by 20 parts of carbon disulfide and 40 parts of 50% sodium hydroxide to yield the corresponding xanthate flour (D.S. 0.17) having a concentration of 47%.

f. One hundred eighty parts of acid-modified starch—90 fluidity—were suspended in 250 parts of water followed by treatment with 40 parts of carbon disulfide and 80 parts of 50% sodium hydroxide solution to yield the corresponding xanthate (D.S. 0.35) having a concentration of 44%.

g. Three hundred sixty parts of acid-modified starch—90 fluidity—were mixed with 300 parts of water followed by 20 parts of carbon disulfide and 40 parts of 50% sodium hydroxide solution to yield the corresponding xanthate (D.S. 0.07) having a concentration of 53%.

h. Pearl corn starch, 81 parts, was suspended in 500 parts of water. Carbon disulfide, 12 parts, and 10 parts sodium hydroxide in 150 parts of water were added to the starch suspension. The suspension was stirred and allowed to stand overnight at 5° C. The resultant starch xanthate (D.S. 0.15) solution had a concentration of 12.9%.

EXAMPLE 2

Sixty-six parts of starch xanthate solution from Example 1(a) were mixed with 4 parts of the herbicide S-propyl dipropylthiocarbamate (6.9% nitrogen), and 3 parts $NaNO_2$. A 10% aqueous solution of acetic acid was added with mixing until the pH of the reaction mixture was 4.2. After standing for 10 minutes at about 25° C. the resulting matrix was filtered, washed with water, and dried at about 25° C. to yield 11.7 parts of product having 2.06% nitrogen. The product contained 30% encapsulated core material. After standing for 40 days at 25° C. in an open container, the product contained 28.7% encapsulated core material.

Although the S-propyl dipropylthiocarbamate core material is very soluble in acetone-hexane mixtures and in acetone alone, these solvents were unable to extract substantial amounts of core material from the encapsulated product. Two parts of the encapsulated product were allowed to stand in 25 parts of an equal volume mixture of hexane and acetone for 5 minutes. The solvent was drained off and the product was allowed to stand in 25 parts acetone for an additional 5 minutes. Nitrogen analysis on the subsequently dried product gave a value of 1.64% (i.e., 23.8% core material). Encapsulation also provides a shield against evaporation losses. Free core material (0.206 part) was placed in an evaporating dish while 0.800 part of the encapsulated product was placed on a second evaporating dish. Both dishes were subjected to the same conditions of temperature and simulated sunlight. After 25 hours there was 100% loss of the free core material, while the nitrogen value of the encapsulated material decreased only from 2.06% to 1.85%, a decrease in the percent of core material of from 30% to 26.8%.

Germination studies, using the above encapsulated product, were performed in 12 containers each containing 50 g. top soil. Eight of the containers (No. 5-12) were treated with 30 mg. of the encapsulated herbicide. On the first day containers 1-4 containing no encapsulated herbicide and containers 5-8 were each planted with 100 grass seeds. On the third day (grass seeds in containers 1-4 had germinated), containers 9-12 were each planted with 100 grass seeds. Each container was watered with 20 ml. of water when the seeds were planted and every 48 hours thereafter. On the tenth day there was no germination in containers 5-8, the grass in containers 9-12 was about 1 inch tall, and the grass in containers 1-4 was about 7-8 inches tall.

EXAMPLE 3

The encapsulation process described in Example 2 was repeated with 51 parts of starch xanthate solution of Example 1(a), 1.5 parts $NaNO_2$, and 1.5 parts of the herbicide, α,α,α-trifluoro-2,6-dinitro-N,N-dipropyl-p-toluidine in 5 parts acetone to yield 14.5 parts of encapsulated product containing 35.6% core material (i.e., 5.17% nitrogen).

EXAMPLE 4

The encapsulation process described in Example 2 was repeated with 40 parts of starch xanthate solution of Example 1(b), 1 part $NaNO_2$, and 3 parts of the insecticide 1,1,1-trichloro-2,2-bis(p-chlorophenyl)ethane (i.e., DDT) to yield 9 parts of encapsulated product containing 16.7% chlorine and 33.4% core material.

EXAMPLE 5

The encapsulation process described in Example 2 was repeated with 42.5 parts of starch xanthate solution of Example 1(c), 3 parts $NaNO_2$, and 4 parts of the insecticide DDT to yield 10.4 parts of encapsulated product containing 19.7% chlorine and 39.4% core material.

EXAMPLE 6

The encapsulation process described in Example 2 was repeated with 23.5 parts of starch xanthate solution of Example 1(d), 1 part $NaNO_2$, and 2.5 parts of the herbicide S-ethyl diisobutylthiocarbamate to yield 6.7 parts of encapsulated product containing 2.0% nitrogen and 31% core material.

EXAMPLE 7

A commercial anionic phosphated starch was treated in the manner described in Example 1 to provide an anionic starch xanthate D.S. 0.35 in a 13.4% aqueous solution.

Forty parts of the anionic starch xanthate solution were mixed with 0.9 part $NaNO_2$ and 8 parts of the insecticide DDT in 15 parts acetone. The mixture was acidified with 5 parts glacial acetic acid, and the resulting insolubilized material was washed with water, filtered, washed with 200 parts hexane, and dried at about 25° C. to yield 11.8 parts of encapsulated product containing 25.8% chlorine and 51.6% core material.

EXAMPLE 8

One part cellulose powder was mixed with 10 parts of an 18% aqueous solution of NaOH and 5 parts carbon disulfide. The reaction mixture was kept at about 25° C. for 4 hours with occasional stirring. The resulting rubbery mass was diluted with 30 parts water and mixed thoroughly with 1 part of the herbicide S-propyl dipropylthiocarbamate (6.9% nitrogen), and 1 part $NaNO_2$. The pH of the mixture was adjusted to 4.5 with 25% aqueous acetic acid. The resulting yellow cake was washed with water and dried at about 25° C. to yield 1.7 parts of a yellow granular material having a sulfur content of 15.5% and a nitrogen content of 1.1%. The product contained 16% encapsulated core material.

EXAMPLE 9

Forty-one parts of starch xanthate solution of Example 1(c) were mixed with 100 parts of water and 3.1 parts of the herbicide S-ethyl diisobutylthiocarbamate followed by the addition of 5 parts of glacial acetic acid and 4 parts of 20% aqueous hydrogen peroxide. After continuation of mixing for 10 minutes the resulting matrix was filtered, washed with water, refiltered, and dried at about 25° C. to yield 11 parts of encapsulated product containing 1.71% nitrogen and 26.6% core material.

EXAMPLE 10

The encapsulation process described in Example 9 was repeated with 45 parts of starch xanthate solution of Example 1(a), 2 parts glacial acetic acid, 2 parts $H_2O_2$, and 4.1 parts of the herbicide S-ethyl diisobutylthiocarbamate to yield a wet cake which was mixed with 10 parts clay. The dried mixture contained 36 parts of product containing 3.8% core material.

EXAMPLE 11

Twenty parts of the herbicide 2,4-dichlorophenoxy acetic acid (2,4-D) was dissolved in 150 parts of absolute ethanol and 18% aqueous sodium hydroxide was added to a pH of about 9. The resulting precipitate (i.e., the sodium salt of 2,4-D) was washed with absolute ethanol and dried.

The encapsulation process described in Example 9 was repeated with 80 parts of starch xanthate solution of Example 1(a), 6 parts 25% aqueous acetic acid (pH of reaction mixture was 5.5), 6 parts of 20% aqueous $H_2O_2$, and 8 parts of the sodium salt of 2,4-D to yield 20 parts of encapsulated product containing 12.7% chlorine and 39.2% core material.

The encapsulated product is odorless in contrast to the free 2,4-D sodium salt or 2,4-D (both have a sharp phenolic odor). In contrast to free 2,4-D or 2,4-D sodium salt, the encapsulated product is stained dark blue when contacted with an aqueous iodine solution.

EXAMPLE 12

The encapsulation process described in Example 9 was repeated with 21 parts of starch xanthate solution of Example 1(a), 2 parts glacial acetic acid, 2 parts ammonium sulfate dissolved in 3 parts water, and 1 part 20% aqueous $H_2O_2$. The insolubilized material was filtered, washed with acetone, and dried at 25° C. to yield 5.7 parts of encapsulated product containing 4.4% nitrogen and 20.6% core material. This product is useful as a slow release fertilizer.

EXAMPLE 13

Seventy-four parts of starch xanthate solution of Example 1(a) were heated to 50° C. and mixed with 2 parts of melted tallow alcohol, 10 parts of 1,2-dibromo-3-chloropropane, 5 parts of glacial acetic acid, and 5 parts of 20% hydrogen peroxide to yield 18.5 parts of encapsulated product containing 33.6% core material.

A sample of 305 mg. after being immersed in water for 3 days was dried to give a product containing 23.8% core material.

EXAMPLE 14

A commercial cationic aminated starch was treated in the manner described in Example 1 to provide a cationic starch xanthate D.S. 0.35 in a 13.4% aqueous solution.

Forty-two parts of cationic starch xanthate were mixed with 5 parts of the sex lure tertiarybutyl 4-chloro-2-methyl cyclohexane carboxylate, 2 parts glacial acetic acid, and 2 parts 20% aqueous $H_2O_2$. The resulting insolubilized material was washed with water, filtered, and dried at about 25° C. to yield 9.8 parts of encapsulated product containing 41.8% core material (by weight increase).

EXAMPLE 15

Eighteen parts of acid-modified corn flour xanthate from Example 1(e) were mixed with 9 parts of 1,2-dibromo-3-chloropropane followed by 4 parts of glacial acetic acid and 2.5 parts of 30% hydrogen peroxide. The insolubilized mixture was mixed with an additional 6.5 parts modified corn flour xanthate from Example 1(e) followed by 0.5 part of 58% sodium nitrite solution and 1.5 parts of glacial acetic acid. The crumbly mass thus obtained was pulverized in a Waring blendor and dried to yield 37 parts of a yellowish powder containing 20% active ingredient.

EXAMPLE 16

Seventy parts of acid-modified starch xanthate from Example 1(f) were mixed with 20 parts of latex SBR 1502 (20% solids) and 15.5 parts of the insecticide 3,3-dimethyl-1-(methylthio)-2-butanone O-[(methylamino)-carbonyl] oxime followed by 9 parts of glacial acetic acid and 4.5 parts of 30% hydrogen peroxide to yield a crumbly mass. The mass was then coated with 14 parts of the acid-modified starch xanthate from Example 1(f) followed by 0.5 part of 58% sodium nitrite solution and 3 parts of glacial acetic acid. The product was ground in a Waring blendor and dried to yield 68 parts of encapsulated product containing 22% active ingredient. The product was then coated with 4 parts of polystyrene dissolved in 20 parts benzene and dried.

EXAMPLE 17

Fifty parts of starch xanthate solution of Example 1(h) were mixed with 10 parts of the herbicide S-ethyl diisobutylthiocarbamate. Into the mixture was stirred a solution of 30% aqueous hydrogen peroxide (0.75 part) and concentrated sulfuric acid (1.3 parts) in ice water (5 parts), wherein the parts are expressed in terms of the total composition. The resulting matrix was recovered in granular form by filtration and drying to yield 14 parts of encapsulated product containing 3.7% nitrogen and 57% core material.

EXAMPLE 18

Three hundred parts of starch xanthate solution of Example 1(h) were mixed with 20 parts of the herbicide S-ethyl diisobutylthiocarbamate. Into the mixture was stirred a solution of 30% aqueous hydrogen peroxide (4.5 parts) and concentrated hydrochloric acid (8 parts) in water (22 parts), wherein the parts are expressed in terms of the total composition. The resulting matrix was recovered in granular form by filtration and drying to yield 53 parts of encapsulated product containing 2.14% nitrogen and 33% core material.

EXAMPLE 19

Three thousand forty-five parts of starch xanthate solution of Example 1(h) were mixed with 55 parts of the herbicide 3-amino-2,5-dichloromethyl benzoate dissolved in 100 parts of acetone. Into the mixture was stirred a solution of 30% aqueous hydrogen peroxide (42 parts) and concentrated sulfuric acid (50.4 parts) in ice water (300 parts), wherein the parts are expressed in terms of the total composition. The resulting matrix was recovered in granular form by filtration and drying to yield 455 parts of encapsulated product containing 3.9% chlorine and 11% core material.

EXAMPLE 20

Eight hundred parts of starch xanthate solution of Example 1(h) were mixed with 10 parts of the herbicide α,α,α-trifluoro-2,6-dinitro-N,N-dipropyl-p-toluidine in melted form. Into the mixture was stirred a solution of 30% hydrogen peroxide (12 parts) and concentrated sulfuric acid (18 parts) in ice water, wherein the parts are expressed in terms of the total composition. The resulting matrix was recovered in granular form by filtration and drying to yield 105 parts of encapsulated product containing 9.5% core material.

EXAMPLE 21

Two thousand six hundred sixty-one parts of starch xanthate solution of Example 1(h) were mixed with 11 parts of the herbicide N-butyl-N-ethyl-α,α,α-trifluoro-2,6-dinitro-p-toluidine dissolved in 60 parts of acetone. A mixture of 75 parts iron sulfate and 27 parts sulfuric acid in 500 parts ice water, wherein the parts are expressed in terms of the total composition, was then added with stirring. The resulting matrix was recovered in granular form by filtration and drying to yield 348 parts of encapsulated product containing 2.1 parts of core material.

We claim:
1. A method of encapsulating a chemical biological agent comprising the steps of:
 a. preparing a dispersion or solution of a suitable chemical biological agent in a matrix-forming material comprising an aqueous solution of a polyhydroxy polymer xanthate (PPX) having a xanthate degree of substitution (D.S.) of from about 0.1 to 3, wherein said solution has a concentration of PPX of from about 5-70%, and wherein the relative amount of said PPX with respect to said biological agent is sufficient to entrap said agent within a matrix of said PPX;
 b. simultaneously adding to said dispersion a strong acid and a coupling agent selected from the group consisting of hydrogen peroxide, ferric sulfate, and ferric chloride, whereby the dispersion is adjusted to a pH of from about 2 to about 7 and whereby said PPX and said coupling agent react from a single phase to form an insolubilized matrix, thereby entrapping said agent; and
 c. recovering said entrapped chemical biological agent.

2. A method as described in claim 1 wherein said strong acid and said coupling agent have been premixed prior to addition to said dispersion.

3. A method as described in claim 1 wherein said strong acid is selected from the group consisting of sulfuric acid, hydrochloric acid, nitric acid, and phosphoric acid.

4. A method as described in claim 1 wherein said strong acid is sulfuric acid and said coupling agent is hydrogen peroxide.

5. A method as described in claim 1 wherein the suitable chemical biological agent is a herbicide, insecticide, fungicide, nematocide, bacteriocide, rodenticide, moluscide, acaricide, larvacide, fumigant, animal repellant, insect repellant, bird repellant, plant growth regulator, fertilizer, pheromone, sex lure, flavor composition, or odor composition.

6. A method as described in claim 1 wherein the suitable chemical biological agent is S-propyl dipropylthiocarbamate, α,α,α-trifluoro-2,6-dinitro-p-toluidine, S-ethyl diisobutylthiocarbamate, 2,6-dichlorobenzonitrile, 1,1'-dimethyl-4,4'-bipyridinium dichloride, 2,4-dichlorophenoxy acetic acid, sodium 2,4-dichlorophenoxy acetate, ammonium 3-amino-2,5-dichlorobenzoate, 3-amino-2,5-dichloromethylbenzoate, 1,2-dibromo-3-chloropropane, O-ethyl-S-phenylethyl phosphorodithioate, S-(1,2-dicarbethoxyethyl)-O,O-dimethyl dithiophosphate, methyl O,O-diethyl-o,p-nitrophenyl phosphorothioate, 1,1,1-trichloro-2,2-bis(p-chlorophenyl)ethane, 2,3-dihydro-2,2-dimethyl-7-benzofuranyl methyl carbamate, methyl 4-allyl-2-methoxyphenol, or tertiarybutyl 4-chloro-2-methyl cyclohexane carboxylate.

7. A method as described in claim 1 wherein the PPX is a xanthate of starch, starch fractions, methyl starch, hydroxyethyl starch, cereal flours, depolymerized flours, cellulose, methyl cellulose, hydroxyethyl cellulose, dextran, dextrin, guar gum, biopolymer gums, cationic starch, anionic starch, or synthetic polyalcohols.

8. A method as described in claim 1 wherein the PPX is a xanthate of starch.

9. A method as described in claim 1 wherein the suitable chemical biological agent in step (a) is present in amounts equal to from about 1% to about 100% of the total amount of the matrix-forming material on a dry weight basis.

* * * * *